(12) United States Patent
Smith et al.

(10) Patent No.: US 11,478,228 B2
(45) Date of Patent: Oct. 25, 2022

(54) SYSTEM AND METHOD FOR BODILY FLUID CAPTURE AND PRESERVATION

(71) Applicant: Dadi Inc., Brooklyn, NY (US)

(72) Inventors: Thomas Smith, Brooklyn, NY (US); Pepin Gelardi, New York, NY (US); Theodore Ullrich, New York, NY (US)

(73) Assignee: Dadi Inc., Brooklyn, NY (US)

( * ) Notice: Subject to any disclaimer, the term of this patent is extended or adjusted under 35 U.S.C. 154(b) by 1007 days.

(21) Appl. No.: 16/196,385

(22) Filed: Nov. 20, 2018

(65) Prior Publication Data
US 2020/0155126 A1 May 21, 2020

(51) Int. Cl.
*A01N 1/02* (2006.01)
*A61B 10/00* (2006.01)
*A61B 17/43* (2006.01)

(52) U.S. Cl.
CPC ...... *A61B 10/0058* (2013.01); *A61B 10/0045* (2013.01); *A61B 10/0096* (2013.01); *A61B 17/43* (2013.01)

(58) Field of Classification Search
None
See application file for complete search history.

(56) References Cited

U.S. PATENT DOCUMENTS

| | | | |
|---|---|---|---|
| 4,530,816 A | 7/1985 | Douglas-Hamilton | |
| 2003/0014982 A1* | 1/2003 | Smith | F25D 11/003 62/480 |
| 2003/0234255 A1* | 12/2003 | Hagopian | B65D 81/3823 220/62.2 |
| 2006/0254944 A1 | 11/2006 | Kao et al. | |
| 2010/0137741 A1 | 6/2010 | Slowey et al. | |
| 2012/0310113 A1 | 12/2012 | Giddings et al. | |
| 2013/0091890 A1 | 4/2013 | Schryver et al. | |

(Continued)

FOREIGN PATENT DOCUMENTS

| FR | 2650256 A1 | 2/1991 |
|---|---|---|
| WO | 2009123889 A1 | 10/2009 |

OTHER PUBLICATIONS

Written Opinion of the International Searching Authority in PCT/US2021/030449 (dated Oct. 7, 2021).

(Continued)

*Primary Examiner* — Paul S Hyun
(74) *Attorney, Agent, or Firm* — Pryor Cashman LLP

(57) ABSTRACT

System and associated method for capturing, preserving, and transporting a bodily fluid, including a collection jar having a base body, a lid body, and a plunger, the plunger housing a preservative when in a first plunger position and permitting a release of the preservative into an internal cavity of the collection jar when in a second plunger position, where the plunger moves from the first plunger position to the second plunger position by pushing the plunger into the internal cavity, and a transportation packaging having an outer container, at least one vacuum insulated panel, at least one phase change material bottle, and at least one collection jar holding tray, where the phase change material bottle has an indented portion corresponding to an indented portion of the collection jar holding tray, where the collection jar is configured for placement in the at least one collection jar holding tray during transportation.

20 Claims, 6 Drawing Sheets

(56) References Cited

U.S. PATENT DOCUMENTS

2014/0342371 A1* 11/2014 Holmes ............ A61B 5/150343
                                                              435/7.1
2017/0000109 A1   1/2017 Xing
2020/0155126 A1   5/2020 Smith et al.

OTHER PUBLICATIONS

International Search Report in PCT/US2021/030449 (dated Oct. 7, 2021).

* cited by examiner

SYSTEM AND METHOD FOR BODILY FLUID CAPTURE AND PRESERVATION

TECHNICAL FIELD

The present invention involves a system and method for capturing and preserving a bodily fluid. More particularly, the present invention involves a system and method for capturing, preserving, and transporting a bodily fluid, such as semen ejaculate, for short or long term storage, subsequent use in in vitro fertilization or other medical procedures and/or testing. Simplicity of use is an important element of the invention as it is intended to be primarily used by ordinary consumers and preservation of the sample is critical, seeking to maintain the same between ejaculation and storage at about 2 degrees to 8 degrees Centigrade.

BACKGROUND OF THE INVENTION

Current means of storing spermatozoa, i.e., sperm or sperm cells, typically involve a remote site for on-premise collection of the specimen, such as at a sperm bank or cryobank. Thus, the interested male must travel to this facility, masturbate while there, and travel back home once finished. This can be time-consuming and uncomfortable, as the interested male must essentially masturbate on command in addition to the facility likely having an unappealing sterile medical ambiance. It would be preferable for the interested male to be able to collect the specimen in the comfort of his home and at his leisure. Yet, of course, preservation of the sample is critical to future use of the same so that collecting at a medical facility is preferred for storage and collecting at one's home is not preferred, at least prior to the present invention. Accordingly, at-home collection kits have been recently developed and available for interested males. However, these kits either have no or poor temperature control elements, such as dry ice packs or cold packs, for maintaining the kit and/or the specimen at an acceptable temperature range or below a maximum. These deficiencies do not adequately consider delays in kit shipment, pick-up, and return, or environmental variations associated with kit destination, e.g., the temperature difference between a user in Minnesota and a user in Florida with storage sites in varying locations with temperatures ranging in those areas. These kits also include numerous components, requiring much more labor and handling by the user and, consequently, leading to greater human error. Therefore, there exists a need for a system and associated method of at-home specimen collection with superior ease of use and precise transportation temperature control.

SUMMARY OF THE INVENTION

In general, in one aspect, the invention features a system for capturing, preserving during transportation, and transporting a bodily fluid in a precise and controlled temperature range, including a collection jar having a base body, a lid body configured to attach to the base body to sealingly close the collection jar, and a plunger disposed on the lid body, the plunger initially housing a preservative when in a first plunger position and permitting a release of the preservative into an internal cavity of the collection jar (just after the specimen is placed therein) when in a second plunger position. The plunger is configured to move from the first plunger position to the second plunger position by a very simple pushing on the plunger inwardly into the internal cavity with the preservative components going into the collection jar and becoming entrained with the sample as a consequence of gravity flow of the preservative.

A transportation packaging kit is provided having an outer container, at least one vacuum-insulated panel component disposed in the outer container, at least one phase change material bottle cradled in the vacuum-insulated panel component, and at least one collection jar holding tray disposed in the phase change material bottle. The phase change material bottle is meant to provide warmth or coolness, as ambient temperature changes so that the sample within the collection jar is maintained at a desired temperature, such as between 2 and 8 degrees Centigrade. The jar holding tray has an indented portion for precisely coupling location of the specimen collection jar during transportation to the long-term storage facility.

Implementations of the invention may include one or more of the following features. A gasket may be disposed on an internal surface of the lid body and configured to seal the collection jar closed when the lid body is attached to the base body. The collection jar may further include a threaded attachment mechanism configured to screw the lid body onto the base body to sealingly close the collection jar. The preservative is meant to preserve the specimen at least during short-term shipment to the storage facility and may include preservative material for long-term storage. Preferably, the preservative may be a commercially available medium including gentamicin, glycerol, and/or albumin. The at least one vacuum-insulated panel may have a bent, elongated U-shaped configuration. The upwardly extending bights of this U-shape provide holding areas for a pair of opposed insulating components. The at least one phase change material bottle is filled with material which will maintain the temperature of the specimen collection jar and its internal contents between about and within a desired temperature range, such as the range of about 2 and 8 degrees Centigrade. The phase change material bottles (2 may be provided) will mate and nest with one another and will then fit within the boundary formed by the U-shaped vacuum-insulated panel and the insulated components held thereby. The phase change material bottles may include a phase change material, such as a commercially available phase change material (PCM) including a functionalized bioPCM, an inorganic material, an organic material, and/or a eutectic material. The transportation package may further include at least one foam endcap disposed in the outer container, and the at least one foam endcap may be composed of a polyurethane foam. The transportation packaging may include two vacuum insulated panels, two phase change material bottles which lie upon, nest, or mate with one another, two collection jar holding trays, and four foam endcaps. Additionally, the outer container may be a hinged box having a first half and a hinged to it second half, and each of the first half and the second half may include one vacuum insulated panel, one phase change material bottle, one collection jar holding tray, and two foam endcaps.

In general, in another aspect, the invention features a method of capturing, preserving, and transporting a bodily fluid, including placing a bodily fluid in an internal cavity of a collection jar, closing the collection jar with the bodily fluid disposed therein, preferably mechanically releasing a preservative into the internal cavity of the collection jar, and placing the collection jar with the bodily fluid and released preservative disposed therein into a transportation packaging, where the collection jar includes a base body, a lid body configured to attach to the base body to close the collection jar, and a plunger disposed on the lid body, the plunger housing the preservative when in a first plunger position and permitting the release of the preservative into the internal cavity of the collection jar for contact with the specimen when in a second plunger position, where the plunger moves from the first plunger position to the second plunger position by inward pushing the plunger into the internal cavity, and where the transportation packaging includes an outer container, at least one vacuum insulated panel disposed in the outer container, at least one phase change material bottle disposed in the outer container, and at least one collection jar holding tray disposed in the outer container, where the phase change material bottle has an indented portion corresponding to an indented portion of the collection jar holding tray, where the collection jar is placed in the at least one collection jar holding tray during transportation.

Implementations of the invention may include one or more of the following features. A gasket may be disposed on an internal surface of the lid body and seal the collection jar closed when the lid body is attached to the base body. The collection jar may further include a threaded attachment mechanism configured to screw the lid body onto the base body to close the collection jar. The preservative may be a commercially available medium including gentamicin, glycerol, and/or albumin. The at least one vacuum-insulated panel may have a bent elongated U-shaped configuration. The at least one phase change material bottle may include a phase change material, such as a commercially available phase change material including a functionalized bioPCM, an inorganic material, an organic material, and/or a eutectic material. The transportation package may further include at least one foam endcap disposed in the legs of the U-shaped vacuum-insulated panel with the at least one foam endcap being composed of a polyurethane foam. The transportation packaging may include two vacuum-insulated panels, two phase change material bottles, two collection jar holding trays, and four foam endcaps. Additionally, the outer shipping and packaging container may comprise a hinged box having a first half and a second half, and each of the first half and the second half may include one of the vacuum-insulated panels, one phase change material bottle, one collection jar holding tray, and two foam endcaps.

DETAILED DESCRIPTION OF THE PREFERRED EMBODIMENTS

The present invention relates to a system and associated method for capturing, preserving, and transporting a bodily fluid, including through the use of a collection jar, an associated sealing lid and a transportation packaging, as will be described herein. The collection jar is preferably configured to collect and hold the bodily fluid and a wash solution which may include a short and/or long term specimen preservative. The collection jar is also preferably configured to easily release the wash solution/preservative into the internal cavity of the jar, such as by a simple, spring-biased upwardly push button mechanism. The transportation packaging is preferably configured to hold the collection jar in a sufficiently stable position during transportation, both to and from a user and the laboratory for testing and short and long term storage facility. The transportation packaging is also preferably configured to maintain the specimen, as preserved, in the collection jar within an acceptable temperature range, preferably but not exclusively between about 2 to 8 degrees Centigrade. The overall process may cover transporting the collection jar in a transportation packaging to a user, removing the collection jar from the transportation packaging, depositing a bodily fluid in the collection jar, releasing the preservative, and transporting the filled collection jar in the transportation packaging to another location, such as a testing laboratory or storage facility. In a preferred embodiment, the bodily fluid is semen ejaculate.

Figure 1:
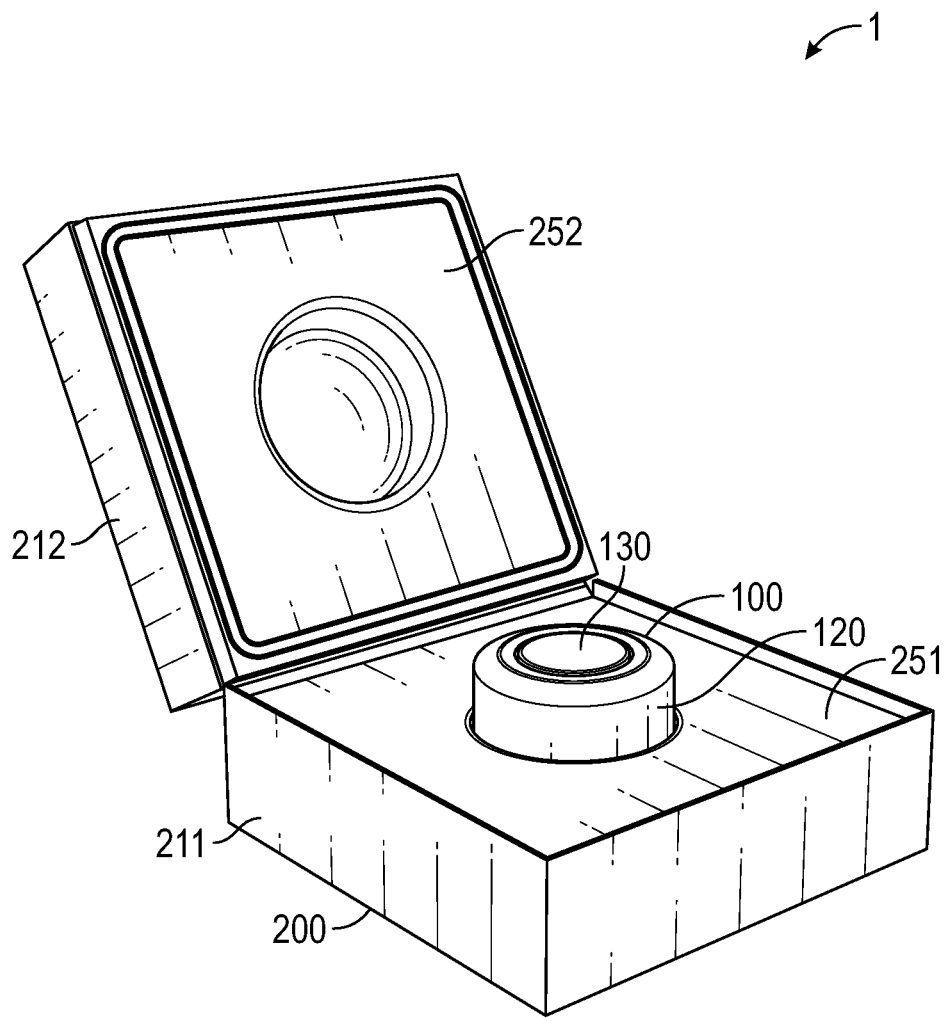
FIG. 1 shows a front perspective view of a system for capturing, preserving, and transporting a bodily fluid according to one embodiment of the present invention, the system comprising a collection jar and transportation packaging.
Figure 2:
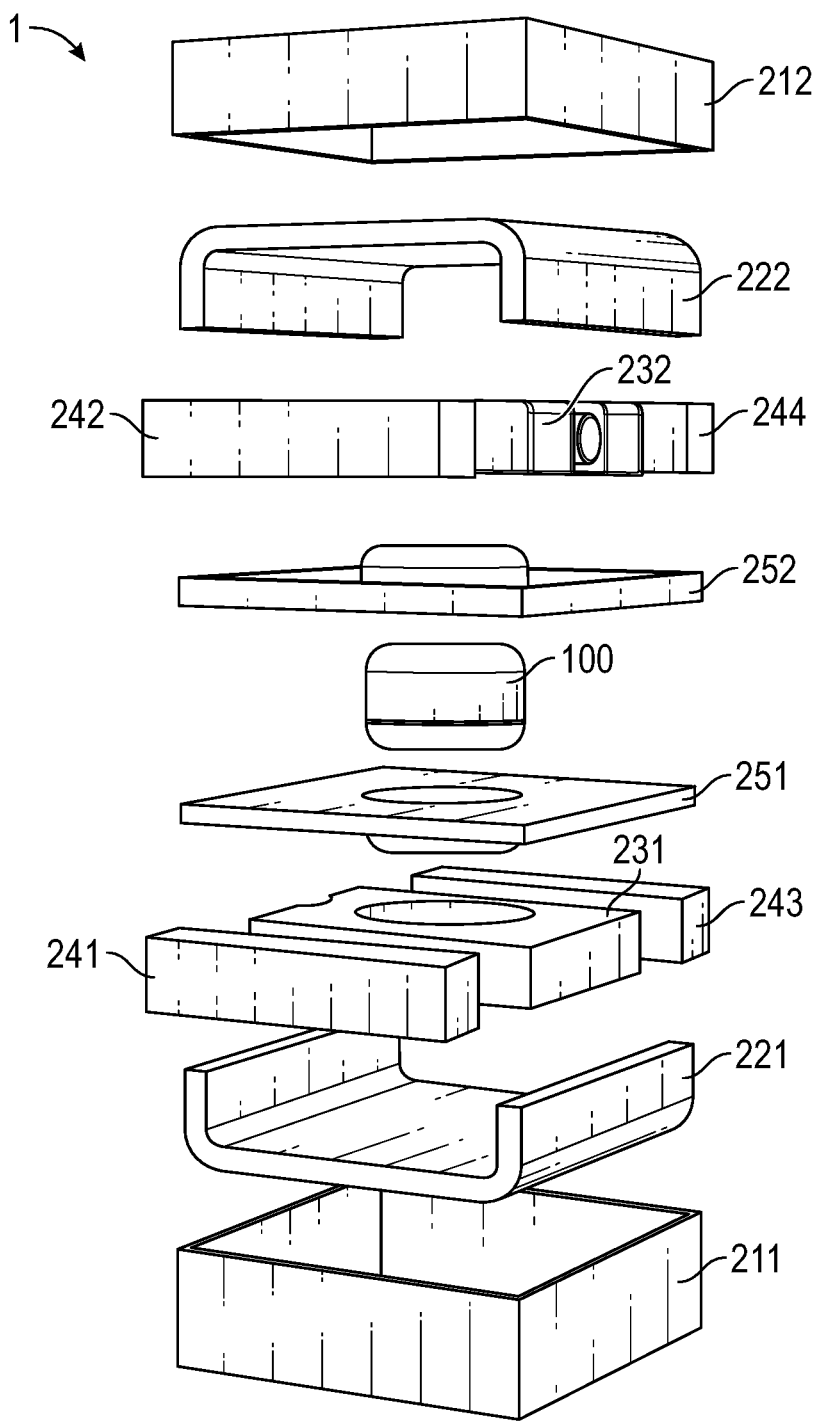
FIG. 2 shows an exploded view of the system of FIG. 1 with the hinge of the top and bottom being separated for ease of illustration.

FIGS. 1 and 2 show different views of a system 1 of the present invention. In this embodiment, system 1 includes a collection jar 100 and a transportation packaging 200. Collection jar 100 may be disposed within, and removed from, transportation packaging 200. As shown, the collection jar 100 is meant to be centrally housed within the transportation packaging 200.

Figure 3:
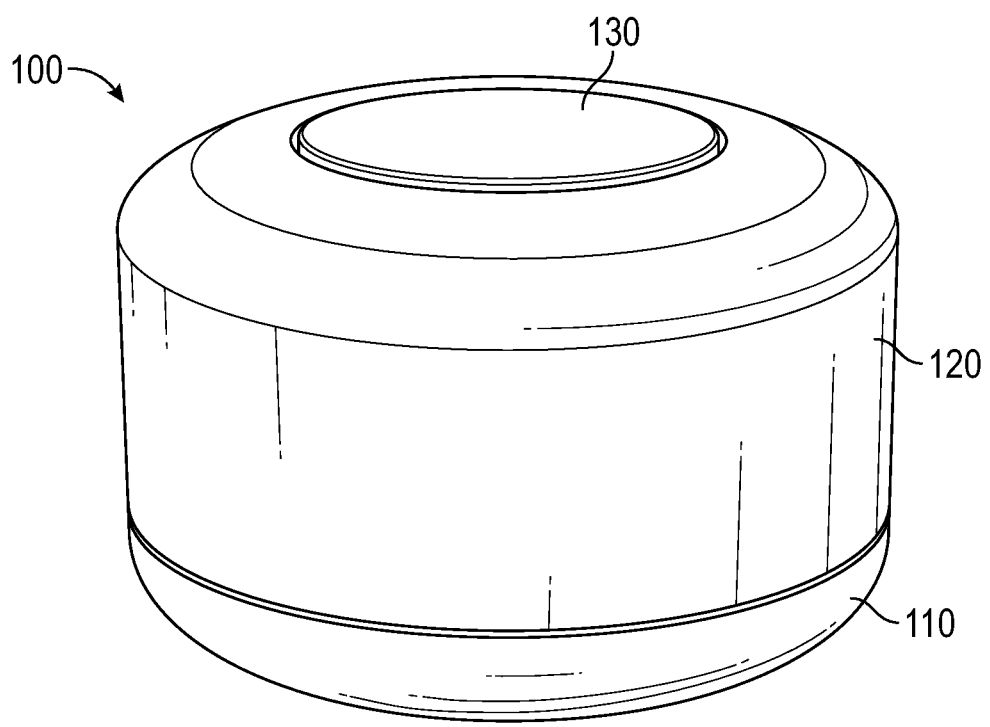
FIG. 3 shows a front view of a collection jar and its lid according to one embodiment of the present invention.
Figure 4:
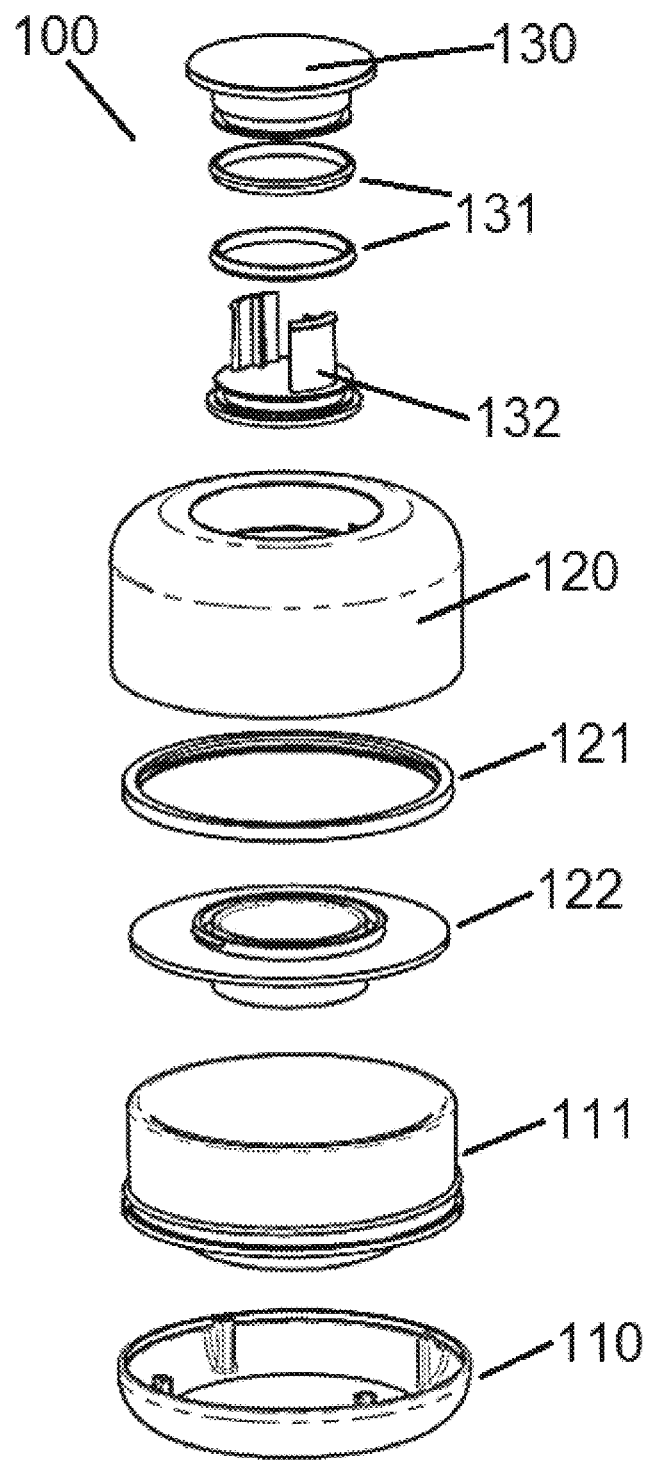
FIG. 4 shows an exploded view of the collection jar and lid, shown in FIG. 3.
Figure 5A:
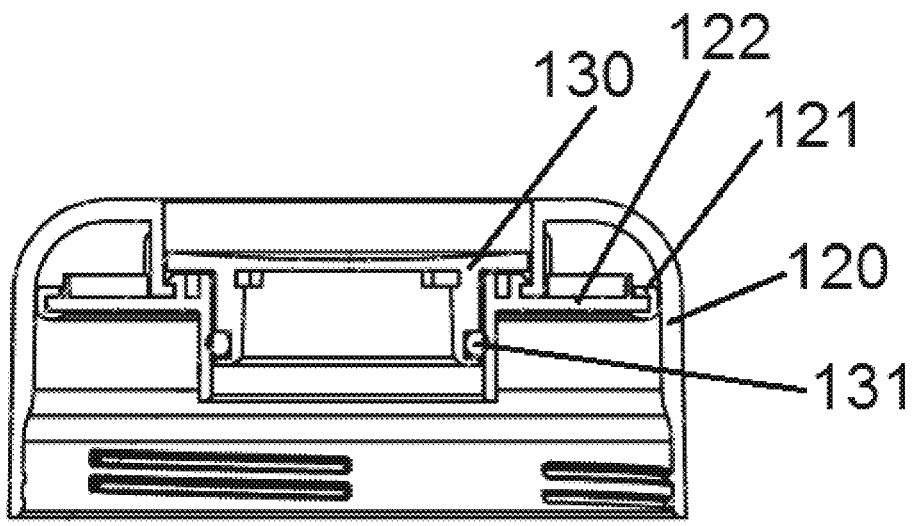
FIGS. 5A-5C show cross-sectional views of components of the collection jar and lid, shown in FIG. 3.
Figure 5B:
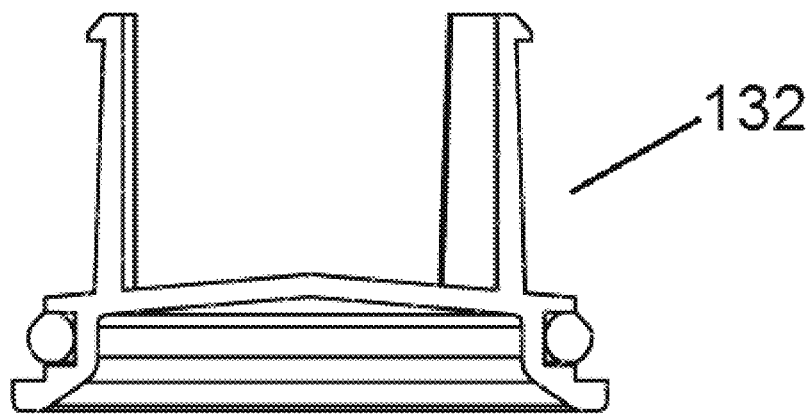
Figure 5C:
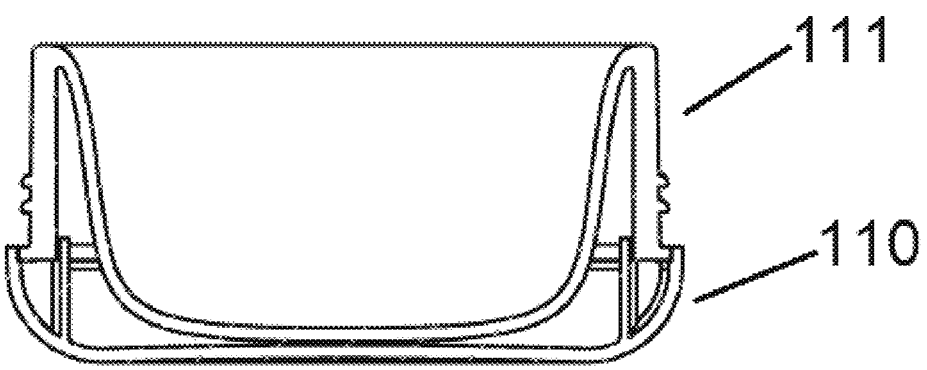

FIGS. 3-5 show several views of a collection jar 100. In FIG. 3, visible elements of collection jar 100 include a base body 110, a lid body 120 that attaches via mating screw threads to base body 110 via its internal container body 111. A plunger button 130 is vertically movingly disposed within lid body 120. A threaded attachment mechanism may be included in collection jar 100 to permit lid body 120 to screw onto base body 110 and internal container body 111 to open and close jar 100. The base body 110 includes a central holding area, similar to many cosmetic holding jars, now commercially available. The lid body 120 mates and closes off the interior of the collection jar. In the exploded view of FIG. 4, collection jar 100 includes base body 110 and an internal container body 111 that connects with base body 110. Internal container body 111 snaps or screws into the base body 110 and provides a central depression area for the specimen. Collection jar 100 also includes outer lid body 120, a lid body gasket 121, and an internal container lid 122. Lid body gasket 121 may be configured to seal collection jar 100 closed when lid body 120 is screwed onto and attached to base body 110. Collection jar 100 also includes plunger button 130, plunger gaskets or O-rings 131, and a plunger 132. Plunger 132 has a flat surface for holding a preservative and a pair of upwardly extending legs which snap into the inside of the plunger button 130. FIG. 5A is a cross-sectional view of lid body 120, FIG. 5B is a cross-sectional view of plunger 132, and FIG. 5C is a cross-sectional view of base body 110.

Plunger 132 may house a substance, such as a wash solution, a preservative, a wash solution containing a preservative, and the like. The substance may include one or more preservatives, nutrients, and/or other compounds for maintaining the health of the bodily fluid for several days, including through return transportation. A selected preservative may be a commercially available medium, such as those including gentamicin, glycerol, and/or albumin, and/or such as those produced by IRVINE SCIENTIFIC (e.g., MULTIPURPOSE HANDLING MEDIUM), VITROLIFE (e.g., SPERMRINSE), COOPERSURGICAL, VETOQUINOL, THERMOFISHER SCIENTIFIC (e.g., Gibco Cell Culture Media), and the like. This substance may be housed on the flat or conical outwardly and downwardly flared surface of the plunger 132 when plunger 132 is in a first position, i.e., plunger button 130 has not been initially pressed or pushed. A user may collect his or her bodily fluid in collection jar 100, such as onto the depression in internal container body 111, and close collection jar 100, such as by screwingly attaching lid body 120 to base body 110. At this point, the user may elect (and will be textually instructed) to release the preservative or wash substance housed in plunger 132. To do so, the user may press or push plunger button 130 to move plunger 132 from the first position to a second position, i.e., the depressed position. The plunger can be spring biased upwardly such that an intentional downward movement on the button 130 will be required to release the material into contact, by gravity flow, with the specimen placed, as mentioned, in the depression of the internal container body 111.

When the plunger is in the second position, an internal cavity or flat or a cone shaped surface of plunger 132 is in fluid communication, i.e., opened to the depression of the internal container body 111. The internal cavity of collection jar 100, such as internal container body 111, and the preservative substance, may secrete from plunger 132 and into the internal cavity of collection jar 100, thereby mixing with the bodily fluid disposed therein. In a preferred embodiment of the present invention, the substance-release mechanism is irreversible, i.e., plunger button 130 can only be pressed once and cannot be reversed from the second plunger position back to the original first plunger position. Or, if it van retract, due to a spring bias of the button, the preservative will have, nevertheless, fallen into and onto the collected specimen.

Figure 6:
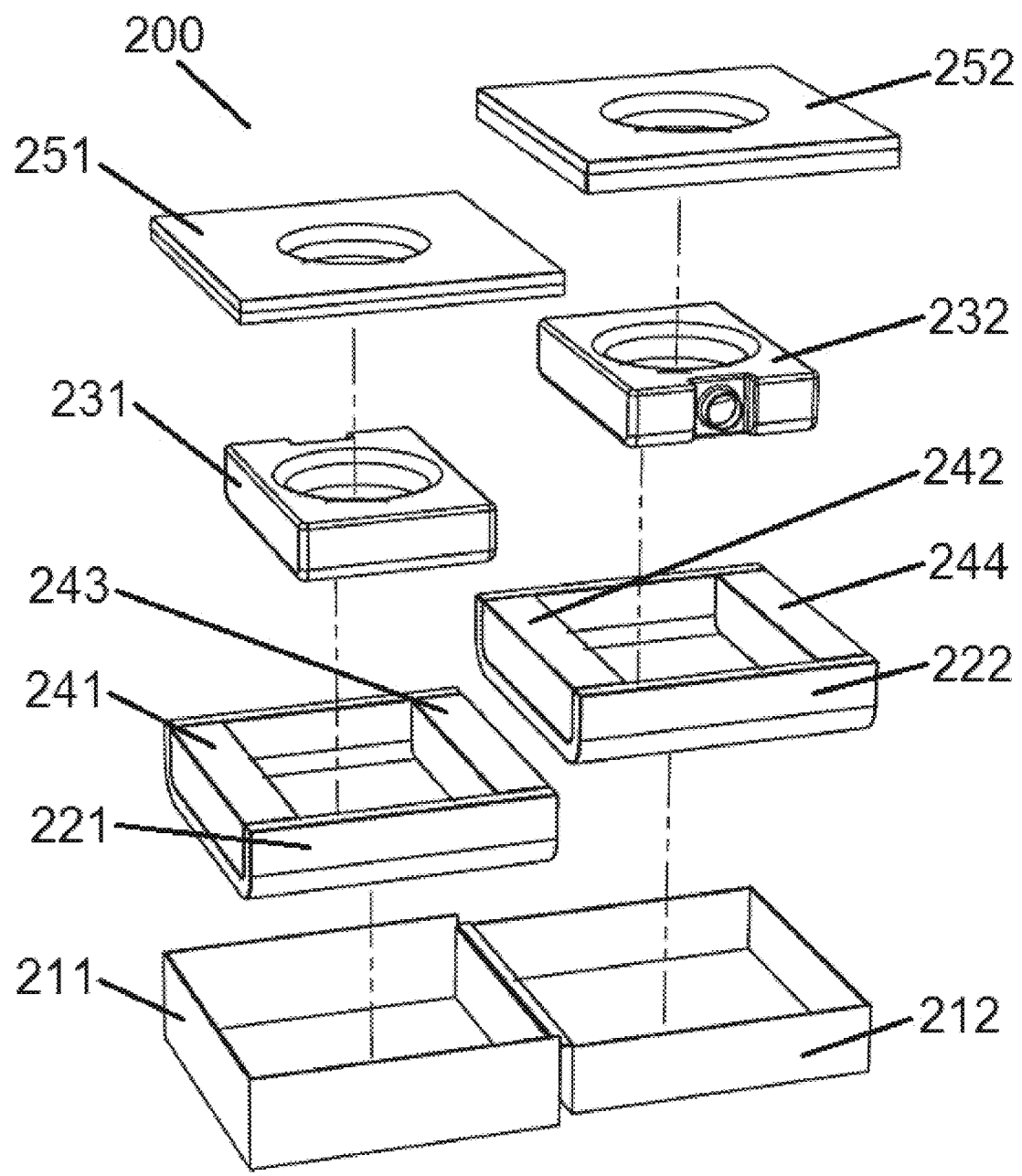
FIG. 6 shows an exploded view of a transportation packaging according to one and the preferred embodiment of the present invention.

FIG. 6 shows an exploded view of a transportation packaging 200. In FIG. 6, transportation packaging 200 includes a first outer container part 211 and a second outer container part 212, which together form the outer container, such as one in the form of a hinged box. Additionally, transportation packaging 200 includes a first assembly disposed in first outer container part 211 that is formed of a vacuum insulated panel 221 and multiple endcaps 241 and 243, and a second assembly disposed in second outer container part 212 that is formed of a vacuum insulated panel 222 and multiple endcaps 242 and 244. Within the first and second assemblies, a phase change material bottle may be disposed, including phase change material bottles 231 and 232, respectively. Collection jar holding trays 251 and 252 may be disposed on the first and second assemblies in first outer container part 211 and second outer container part 212, respectively.

Collection jar holding trays 251 and 252 are preferably configured to hold or cradle, including during transportation, collection jar 100 within a centrally recessed or indented portion of trays 251 and 252. Phase change material bottles 231 and 232 may also have a corresponding centrally recessed or indented portion such that indented portions of trays 251 and 252 are disposed in indented portions of phase change material bottles 231 and 232, respectively. A phase change material is preferably disposed in phase change material bottles 231 and 232, and the selected phase change material may be a commercially available phase change material, including but not limited to a functionalized bioPCM, an inorganic material, an organic material, a eutectic material. In one embodiment, it is preferable that the phase change material be selected such that a preservative housed in collection jar 100 is maintained at a desired temperature, such as a temperature of less than or equal to 72° F., and a bodily fluid-preservative mixture housed in collection jar 100 is maintained at a desired temperature, such as a temperature in the range of 68-72° F., during return transportation. In another embodiment, the desired temperature range is between about 2 to 8 degrees Centigrade. The desired temperature range may be any acceptable temperature range and may be determined based on the substance or object being housed and transported as well as the associated phase change material selected for this substance or object.

Vacuum insulated panels 221 and 222 may have a bent U-shaped configuration or orientation. This shape permits phase change material bottles, such as bottles 231 and 232, to be encased in the vacuum insulated panels, such as panels 221 and 222, thereby eliminating or reducing thermal leakage at side portions. Additionally, endcaps 241, 242, 243, and 244 may be composed of a polyurethane foam.

While a primary application of the system and associated method of the present invention is the collection and transportation of semen ejaculate, this system and method may be utilized with respect to other bodily fluids that can be collected through home use and that benefit from greater temperature control during transportation, either to or from the user. Other bodily fluids and the like may include amniotic fluid, aqueous humour, vitreous humour, bile, blood, blood phasma, blood serum, cerebrospinal fluid, cerumen or earwax, chyle, chyme, endolymph, perilymph, exudates, feces, female ejaculate, gastric acid, gastric juice, lymph, mucus, pericardial fluid, peritoneal fluid, pleural fluid, pus, rheum, saliva, sebum or skin oil, serous fluid, semen, serum, smegma, sputum, synovial fluid, sweat, tears, urine, vaginal secretion, vaginal discharge, vomit, cord blood, and stem cells. Additionally, this system and method may be utilized in non-human applications, e.g., for animal bodily fluids, including but not limited to horse or bull semen. Additionally, this system and method may be utilized in non-medical applications involving multiple transportations with a need for greater temperature control, such as meats, beverages, and luxury goods at risk of damage by extreme temperatures.

The embodiments and examples above are illustrative, and many variations can be introduced to them without departing from the spirit and scope of the disclosure or from the scope of the invention. For example, elements and/or features of different illustrative and exemplary embodiments herein may be combined with each other and/or substituted with each other within the scope of this disclosure. For a better understanding of the invention, its operating advantages and the specific objects attained by its uses, reference should be had to the drawings and descriptive matter, in which there is illustrated a preferred embodiment of the invention.

What is claimed is:

1. A system for capturing, preserving, and transporting a bodily fluid, comprising:
   a collection jar comprising:
      a base body;
      a lid body configured to attach to the base body;
      a plunger disposed on the lid body, the plunger housing a preservative when in a first plunger position and permitting a release of the preservative into an internal cavity of the collection jar when in a second plunger position; and
   the preservative;

wherein the plunger is configured to move from the first plunger position to the second plunger position by pushing the plunger into the internal cavity; and a transportation packaging comprising:
an outer container;
at least one vacuum insulated panel disposed in the outer container;
at least one phase change material bottle disposed in the outer container;
and at least one collection jar holding tray disposed in the outer container;
wherein the phase change material bottle has an indented portion corresponding to an indented portion of the collection jar holding tray;
wherein the collection jar is configured for placement in the at least one collection jar holding tray during transportation.

2. The system of claim 1, wherein a gasket is disposed on an internal surface of the lid body.

3. The system of claim 1, wherein the collection jar further comprises a threaded attachment mechanism configured to screw the lid body onto the base body.

4. The system of claim 1, wherein the preservative is a commercially available medium comprising gentamicin, glycerol, and/or albumin.

5. The system of claim 1, wherein the at least one vacuum insulated panel has a bent U-shaped configuration.

6. The system of claim 1, wherein the at least one phase change material bottle includes a phase change material, and wherein the phase change material is a commercially available phase change material comprising a functionalized bioPCM, an inorganic material, an organic material, and/or a eutectic material.

7. The system of claim 1, wherein the transportation package further comprises at least one foam endcap disposed in the outer container.

8. The system of claim 7, wherein the at least one foam endcap is composed of a polyurethane foam.

9. The system of claim 7, wherein the transportation packaging comprises two vacuum insulated panels, two phase change material bottles, two collection jar holding trays, and four foam endcaps.

10. The system of claim 9, wherein the outer container is a hinged box having a first half and a second half, and wherein each of the first half and the second half includes one vacuum insulated panel, one phase change material bottle, one collection jar holding tray, and two foam endcaps.

11. A method of capturing, preserving, and transporting a bodily fluid, comprising:
placing a bodily fluid in an internal cavity of a collection jar;
closing the collection jar with the bodily fluid disposed therein;
releasing a preservative into the internal cavity of the collection jar; and
placing the collection jar with the bodily fluid and released preservative disposed therein into a transportation packaging;
wherein the collection jar comprises:
a base body;
a lid body configured to attach to the base body;
a plunger disposed on the lid body, the plunger housing the preservative when in a first plunger position and permitting the release of the preservative into the internal cavity of the collection jar when in a second plunger position; and
the preservative;
wherein the plunger moves from the first plunger position to the second plunger position by pushing the plunger into the internal cavity; and
wherein the transportation packaging comprises:
an outer container;
at least one vacuum insulated panel disposed in the outer container;
at least one phase change material bottle disposed in the outer container;
and at least one collection jar holding tray disposed in the outer container;
wherein the phase change material bottle has an indented portion corresponding to an indented portion of the collection jar holding tray;
wherein the collection jar is placed in the at least one collection jar holding tray during transportation.

12. The method of claim 11, wherein a gasket is disposed on an internal surface of the lid body.

13. The method of claim 11, wherein the collection jar further comprises a threaded attachment mechanism configured to screw the lid body onto the base body.

14. The method of claim 11, wherein the preservative is a commercially available medium comprising gentamicin, glycerol, and/or albumin.

15. The method of claim 11, wherein the at least one vacuum insulated panel has a bent U-shaped configuration.

16. The method of claim 11, wherein the at least one phase change material bottle includes a phase change material, and wherein the phase change material is a commercially available phase change material comprising a functionalized bioPCM, an inorganic material, an organic material, and/or a eutectic material.

17. The method of claim 11, wherein the transportation package further comprises at least one foam endcap disposed in the outer container.

18. The method of claim 17, wherein the at least one foam endcap is composed of a polyurethane foam.

19. The method of claim 17, wherein the transportation packaging comprises two vacuum insulated panels, two phase change material bottles, two collection jar holding trays, and four foam endcaps.

20. The method of claim 19, wherein the outer container is a hinged box having a first half and a second half, and wherein each of the first half and the second half includes one vacuum insulated panel, one phase change material bottle, one collection jar holding tray, and two foam endcaps.

* * * * *